United States Patent [19]

Suzuki et al.

[11] Patent Number: 4,859,457
[45] Date of Patent: Aug. 22, 1989

[54] HAIR RINSE COMPOSITION

[75] Inventors: Toshio Suzuki, Ichikawa; Takeo Okumura, Funabashi, both of Japan

[73] Assignee: Kao Corporation, Tokyo, Japan

[21] Appl. No.: 627,837

[22] Filed: Jul. 5, 1984

[30] Foreign Application Priority Data

Jul. 12, 1983 [JP] Japan .................. 58-126390

[51] Int. Cl.$^4$ .................... A61K 7/06; A61K 7/08
[52] U.S. Cl. ........................ 424/70; 424/78; 424/80
[58] Field of Search .......................... 424/70

[56] References Cited

U.S. PATENT DOCUMENTS

| 2,192,907 | 3/1940 | Harris | 424/365 |
| 3,959,461 | 5/1976 | Bailey | 424/365 |
| 4,165,369 | 8/1979 | Watanabe et al. | 424/70 |

FOREIGN PATENT DOCUMENTS

| 757957 | 4/1971 | Belgium | 424/70 |
| 135234 | 10/1979 | Japan | 424/70 |
| 0079317 | 6/1980 | Japan | 424/70 |
| 169614 | 12/1981 | Japan | 424/70 |
| 109707 | 8/1982 | Japan | 424/70 |
| 109708 | 8/1982 | Japan | 424/70 |
| 109710 | 8/1982 | Japan | 424/70 |
| 0827063 | 5/1981 | U.S.S.R. | 424/70 |
| 2078744 | 1/1982 | United Kingdom | 424/70 |

OTHER PUBLICATIONS

Kirk-Othmer, Encyclopedia of Chemical Technology, *Electron Tube Materials to Ferrites*, vol. 8, 2nd ed. (1965), p. 152.

Japanese Official Action dated Aug. 10, 1988 relative to Japanese Application No.: 126390/1983.

*Primary Examiner*—Dale R. Ore
*Attorney, Agent, or Firm*—Oblon, Spivak, McClelland, Maier & Neustadt

[57] ABSTRACT

A hair rinse composition having improved rinsing performance and a process specified to prepare the same.

The composition according to the invention comprises (A) 0.05 to 0.5 wt % of cationic surface active agent, and (B) a higher alcohol or a glycerine mono fatty acid ester having a melting point not lower than 45° C. The ingredient (B) should be contained in an amount of 3 to 15 times by weight to ingredient (A).

The composition is prepared by diluting a highly concentrated emulsified product containing 0.4 to 34 wt % of ingredient (A) and (B) in total with 1 to 20 times by weight to the emulsified product of water.

10 Claims, No Drawings

HAIR RINSE COMPOSITION

BACKGROUND OF THE INVENTION

1. Field of the Invention

This invention relates to novel hair rinse compositions and more particularly, to hair rinse compositions which comprise a minor proportion of cationic surface active agents and a major proportion of oils, but free of hydrophilic nonionic surface active agents. Such hair rinse compositions have good stability and high rinsing performance.

2. Description of the Prior Art:

Various troubles after hair washing have been heretofore removed by rinsing the hair with hair rinse compositions which comprise 1 to 5 wt % (hereinafter referred to simply as %) of quaternary ammonium salts such as distearyldimethylammonium chloride as the effective component thereof.

The hair rinse is used to impart to hair flexibility, smoothness, antistaticity and the like, but use of quaternary ammonium salts alone is not sufficient to give satisfactory performances on the flexibility and smoothness. In order to avoid the drawback, it is general to further add oils such as higher alcohols, glycerides, liquid paraffins and the like. Since, however, quaternary ammonium salts have no ability of stably emulsifying or dispersing oils in amounts sufficient to show their performances, attempts were made to add nonionic active agents of higher hydrophilicity so as to stabilize the dispersion system. Highly hydrophilic nonionic active agents have the action of considerably lowering the rinsing performance. Hair rinses which comprise quaternary ammonium salts, oils, and nonionic surface active agents of high hydrophilicity do not show satisfactory rinsing performances. On the other hand, cationic surface active agents are able to stably emulsify several or larger times of oils but it was difficult to obtain hair rinse compositions with excellent rinsing performances using such cationic active agents.

Thus, known hair rinse compositions are not necessarily satisfactory with respect to the rinsing performances, i.e. performances of imparting to hair flexibility, smoothness, and antistaticity, and there is a demand of the development of hair rinse compositions of better performances.

SUMMARY OF THE INVENTION

We have made intensive studies to overcome the drawbacks of the prior art hair rinses and, as a result, found that hair rinse compositions of good rinsing performances can be obtained by first preparing an emulsion of high concentration from a small amount of a cationic surface active agent and a specific type of oil, and diluting the emulsion with water whereby the oil can be stably emulsified in large amounts without use of an nonionic surface active agent of high hydrophilicity.

According to the present invention, there is provided a hair rinse composition which comprises (A) 0.05 to 0.5 wt % of a cationic surface active agent, and (B) a higher alcohol or a glycerine mono fatty acid ester having a melting point not lower than 45° C. and contained in an amount of 3 to 15 times by weight to ingredient (A), and said composition is produced by diluting a highly concentrated emulsified product containing 0.4 to 34 wt % of ingredient (A) and (B) in total with 1 to 20 times by weight to the emulsified product of water.

DETAILED DESCRIPTION OF THE INVENTION AND PREFERRED EMBODIMENTS

The cationic surface active agent which is ingredient (A) of the invention is not limited to any specific ones. All cationic surface active agents which are ordinarily used in hair rinse agents may be used in the practice of the invention. Preferable quaternary ammonium salts are those having the following formula (I):

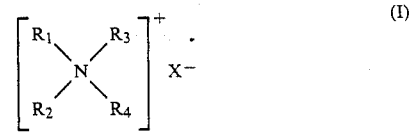

in which one or two of $R_1$, $R_2$, $R_3$, and $R_4$ independently represent a linear or branched alkyl or hydroxyalkyl group having from 8 to 22 carbon atoms, the others independently represent an alkyl group having from 1 to 3 carbon atoms, hydroxyalkyl group, benzyl group, or polyoxyethylene group in which the total number of added moles is not larger than 10, and X represents a halogen atom or alkylsulfate group having 1 to 2 carbon atoms.

Of the quaternary ammonium salts, the following compounds are more preferable:
distearyldimethylammonium chloride,
stearyltrimethylammonium methosulfate,
stearyltrimethylammonium chloride,
stearyldimethylbenzylammonium chloride,
docosyltrimethylammonium methosulfate,
docosyltrimethylammonium chloride,
docosyldimethylbenzylammonium chloride,
didocosyldimethylammonium chloride,
lauryldiethylbenzylammonium chloride,
lauryltrimethylammonium bromide,
distearylmethylhydroxymethyl chloride,
cetyltrimethylammonium chloride, N-stearyl-N,N,N-tri(polyoxyethylene)ammonium chloride (3 moles added in total), cetyltriethylammonium bromide, stearyldimethylammonium chloride and the like.

The ingredient (A) is generally added in an amount of from 0.05 to 0.5 wt % of the total composition. Outside the range, a satisfactory rinsing performance cannot be achieved.

The higher alcohols which are ingredient (B) are alcohols having a linear or branched alkyl or alkenyl group containing from 12 to 26 carbon atoms. Preferable examples include cetostearyl alcohol (mixture of cetyl alcohol and stearylalcohol), cetyl alcohol, arachidic alcohol, behenyl alcohol, calnabil alcohol, ceryl alcohol and the like.

The glycerine monofatty acid esters are represented by the following general formula (II)

in which $R_5$ represents a linear or branched hydrocarbon group having from 11 to 23 carbon atoms. Preferable examples are glycerides composed mainly of oleic acid monoglyceride, palmitic acid monoglyceride, isostearic acid monoglyceride, stearic acid monoglyceride, behenic acid glyceride, and the like. Commercially available products called monoglycerides usually contain, aside from monoesters, large amount of diesters, triesters and unreacted glycerine and are not suitable for the purpose of the invention. In order to yield good rinsing performances, it is necessary that not lower than 80% of glycerine monofatty acid esters indicated above be contained. The ingredient (B) used in the present invention should have a melting point not lower than 45° C. The esters whose melting temperature is lower than 45° C. are more oleophilic and cannot give good feeling to the touch.

The amount of ingredient (B) is preferably in the range from 3 to 15 times as large as the ingredient (A). Less amounts do not show any appreciable rinsing performance, whereas larger amounts are unfavorable in that stable emulsification is not accomplished.

The water-soluble polymer compounds used as the ingredient (C) are, for example, cellulose derivatives, polyvinyl alcohol, polyvinylpyrrolidone, sodium polyacrylate, carboxyvinyl polymer, polyethyleneimine, and the like.

Of these, there are preferred cellulose derivatives of the formula (III)

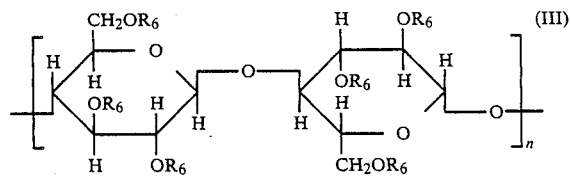

in which $R_6$s independently represent hydrogen, $-(CH_2CH_2O)_m-H$, $-(CH_2CH_2CH_2O)_m-H$ (wherein m is an integer of from 1 to 5), $-CH_3$, $-C_2H_5$, or $-COONa$, and n is an integer of from 5 to 5000. Most preferably, hydroxyethylcellulose and hydroxymethylcellulose are used.

The ingredient (C) does not show its performance when used in amounts less than 0.1%, and any further performance cannot be expected when the amounts exceed 5%. Accordingly, the amount ranging from 0.1 to 5% is preferable.

The stable hair rinse composition of the invention cannot be obtained merely by emulsifying ingredients (A) and (B), or ingredients (A), (B) and (C) in the defined ranges of amounts in water. In order to obtain the hair rinse composition of the invention, 0.1 to 9% of ingredient (A) and ingredient (B) in an amount of 3 to 15 times by weight as large as the ingredient (A) are added to water in such a way that the total amount of both ingredients reaches 0.4 to 34%, followed by heating under agitation to prepare a highly concentrated emulsion. Subsequently, the emulsion was diluted with 1 to 20 times by weight, preferably 2 to 15 times by weight, as large as water so that the content of ingredient (A) is within the above-defined range (0.05 to 0.5%). Ingredient (C) is preferably used after dispersion in water. The hair rinse composition may further comprise humectants, perfumes, colorants and the like which are ordinary used for these purposes, if necessary.

The thus obtained hair rinse composition of the invention are stable under either low temperature or high temperature conditions, with very good rinsing performances.

The present invention is illustrated by way of examples, which should not be construed as limiting the present invention thereto. In examples, the following test methods were used.

(1)

Appearance

A sample was placed in a 100 ml transparent glass container and its appearance was visually observed. It will be noted that if a sample had bubbles therein, it was subjected to centrifugal separator for defoaming.
O=homogeneous; separation or coagulation is not observed.
X=heterogeneous; separation and/or coagulation is observed.

(2)

High temperature stability

A sample was placed in a transparent glass container, tightly sealed, and kept in a thermostatic chamber of 50° C. for one month. Thereafter, phase separation of the sample was visually observed.
O=homogeneous; separation or coagulation is not observed.
X=heterogeneous; separation and/or coagulation is observed.

(3)

Low temperature stability A sample was placed in a transparent glass container, tightly sealed, and kept in a thermostatic chamber of −5° C. for one month. Thereafter, separation or solidification were visually observed.
O=homogeneous; separation or coagulation is not observed.
X=heterogeneous; separation and/or coagulation is observed.

(4)

Emulsified state

A highly concentrated emulsion which was cooled to room temperature was observed visually or through microscope. Moreover, 5 g of the highly concentrated emulsion was placed in 100 ml of water and agitated at a normal temperature for 1 hour, after which the dispersed state of the resulting emulsion was observed.
O=Uniform in particle size and uniformly dispersed in water.
X=Non-uniform in particle size and not uniformly dispersed in water.

(5)

Rinsing performance and organoleptic evaluation

Five hundreds ml of 1:50 dilutions of the respective hair rinses and a commercially available hair rinse were each used to treat hair therewith, followed by rinsing twice with warm water and air drying. The hair was organoleptically evaluated with respect to the softness, smoothness and combing ease. In comparison with the commercially available hair rinse, the hair rinses of the invention are evaluated as follows.
⊙=more excellent, O=better, Δ=equal, and X=poorer.

EXAMPLE 1

Compositions of the formulations indicated in Table 1 were prepared and used to determine their appearance, stability, and rinsing performance. Preparation of Composition:

To water (1) heated to 70° C. were added ingredients (A) and (B) heated to and dissolved at the same temperature as indicated above, followed by agitating for emulsification and cooling to room temperature while agitating. After the cooling, water (2) was added to the mixture while agitating. After the cooling, water (2) was added to the mixture while agitating, thereby obtaining the respective compositions.

Results: as shown in Table 1.

TABLE 1

| Composition (%) | Product of Invention | | | Comparative Product | | |
|---|---|---|---|---|---|---|
| | 1 | 2 | 3 | 1 | 2 | 3 |
| Ingredient (A) | | | | | | |
| Stearyltrimethylammonium chloride | 0.5 | 0.2 | 0.05 | 0.8 | 0.5 | 0.05 |
| Ingredient (B) | | | | | | |
| Behenyl alcohol | 2.1 | 2.5 | 0.15 | 1.0 | 1.0 | 1.0 |
| Water (1) | 5.73 | 7.3 | 4.80 | 3.2 | 8.5 | 3.95 |
| Ratio of Ingredient (B) and Ingredient (A) [(B)/(A)] | 4.20 | 12.5 | 3.0 | 1.25 | 2.0 | 20.0 |
| Emulsified state | O | O | O | O | O | X |
| Water (2) (water for dilution) | 91.67 | 90.0 | 95.0 | 95.0 | 90.0 | 95.0 |
| Appearance | O | O | O | O | O | X |
| Stability | | | | | | |
| High temperature stability | O | O | O | O | O | X |
| Low temperature stability | O | O | O | O | O | X |
| Rinsing performance | | | Δ | X | X | X |

EXAMPLE 2

To water (1) heated to 70° C. were added stearyltrimethylammonium chloride (ingredient A), behenyl alcohol (ingredient B), and propylene glycol, which were heated to and dissolved at the same temperature as indicated above, followed by agitating for emulsification and cooling to room temperature under agitation. The products of the invention were obtained by further adding water (2) to the mixture under agitation, thereby giving dilutions. The results are shown in Table 2.

TABLE 2

| Composition (%) | Comparative Products | | | | | Products of Invention | | | | | |
|---|---|---|---|---|---|---|---|---|---|---|---|
| | 4 | 5 | 6 | 7 | 8 | 4 | 5 | 6 | 7 | 8 | 9 |
| Stearyltrimethylammonium chloride | 0.2 | 0.1 | 0.2 | 0.2 | 0.2 | 0.2 | 0.2 | 0.2 | 0.2 | 0.2 | 0.2 |
| Benhenyl alcohol | 0.2 | 1.0 | 2.0 | 3.0 | 0.2 | 1.0 | 2.0 | 3.0 | 1.0 | 2.0 | 3.0 |
| Propylene glycol | 0.5 | 0.5 | 0.5 | 0.5 | 0.5 | 0.5 | 0.5 | 0.5 | 0.5 | 0.5 | 0.5 |
| Water (1) | 99.1 | 98.4 | 97.3 | 96.3 | 32.8 | 31.6 | 30.6 | 29.6 | 8.3 | 7.3 | 6.3 |
| Water (2) | 0 | 0 | 0 | 0 | 66.3 | 66.7 | 66.7 | 66.7 | 90 | 90 | 90 |
| Appearance | X | X | X | X | X | O | O | O | O | O | O |
| High temperature stability | X | X | X | X | X | O | O | O | O | O | O |
| Low temperature stability | X | X | X | X | X | O | O | O | O | O | O |

EXAMPLE 3

To water (1) heated to 70° C. (with comparative products, a water-soluble polymer was dispersed in water) were added ingredients (A) and (B) and propylene glycol heated to and dissolved at the same temperature as indicated above, followed by agitating for emulsification and cooling to room temperature under agitation. With the products of the invention, water (2) in which a water-soluble polymer was dispersed was added for dilution to the cooled emulsion, thereby obtaining compositions of the invention. The results are as shown in Table 3.

TABLE 3

| Composition (%) | Comparative Products | | | Products of Invention | | | |
|---|---|---|---|---|---|---|---|
| | 9 | 10 | 11 | 10 | 11 | 12 | 13 |
| Ingredient (A) | | | | | | | |
| Stearyltrimethylammonium chloride | 0.2 | 0.2 | | 0.2 | 0.2 | | 0.2 |
| Distearyldimethylammonium chloride | | | 0.2 | | | 0.2 | 0.2 |
| Ingredient (B) | | | | | | | |
| Cetostearyl alcohol | 2.0 | | | 2.0 | | | 2.0 |
| Cetyl alcohol | | 2.0 | | | 2.0 | | |
| Stearic acid monoglyceride | | | 2.0 | | | 2.0 | |
| Water-soluble Polymer | | | | | | | |
| Hydroxyethyl cellulose | | | | 0.4 | 0.4 | 0.4 | 0.4 |
| Hydroxymethyl cellulose | 0.4 | 0.4 | 0.4 | | | | |
| Propylene glycol | 1.0 | 1.0 | 1.0 | 1.0 | 1.0 | 1.0 | 1.0 |
| Water (1) | 96.4 | 96.4 | 96.4 | 16.8 | 16.8 | 16.8 | 15.4 |
| Water (2) (water for dilution) | 0 | 0 | 0 | 79.6 | 79.6 | 79.6 | 80.8 |
| Appearance | X | X | X | O | O | O | O |
| Stability | | | | | | | |
| High temperature stability | X | X | X | O | O | O | O |
| Low temperature stability | X | X | X | O | O | O | O |

EXAMPLE 3

Rinse compositions were prepared in the same manner as in Example 3. The results are shown in Table 4.

TABLE 4

|  | Comparative Product 12 | Invention Product 14 | Invention Product 15 | Comparative Product 13 | Invention Product 16 | Invention Product 17 | Comparative Product 14 |
|---|---|---|---|---|---|---|---|
| Ingredient A | | | | | | | |
| Stearyltrimethylammonium Chloride | 0.3 | 0.3 | 0.3 | 0.3 | 0.3 | 0.3 | 0.3 |
| Ingredient (B) | | | | | | | |
| Cetostearyl Alcohol | 2.0 | 2.0 | 2.0 | | | | |
| Cetyl Alcohol | — | — | — | 2.0 | 2.0 | — | — |
| Behenyl alcohol | | | | | | 2.0 | 2.0 |
| Water-soluble Polymer | | | | | | | |
| Hydroxyethyl Cellulose | | | | 0.2 | 0.2 | 0.2 | 0.2 |
| Hydroxymethyl Cellulose | 0.2 | 0.2 | 0.2 | | | | |
| Propylene Glycol | 0.5 | 0.5 | 0.5 | 0.5 | 0.5 | 0.5 | 0.5 |
| Water (1) | 97 | 30.3 | 17.0 | 97 | 17.0 | 17.0 | 3.6 |
| Water (2) (water for dilution) | 0 | 66.7 | 80.0 | 0 | 80.0 | 80.0 | 93.4 |
| Appearance | X | O | O | X | O | O | X |
| Stability | | | | | | | |
| High Temperature Stability | O | O | O | O | O | O | O |
| Low Temperature Stability | O | O | O | O | O | O | O |
| Organoleptic Evaluation | | | | | | | |
| Softness | X | O | | X | O | | X |
| Smoothness | Δ | | | Δ | | | Δ |
| Ease in Combing | X | | | X | | | X |

EXAMPLE 5

Hair rinse compositions of the following formulations were prepared and 500 ml of a 1:50 dilution of each composition was used to treat hair therewith, followed by rinsing twice with warm water and air drying. The compositions were evaluated by 20 panelists using the Sheffe's paired comparison by five ranks. The results are shown in Table 5.

Product No. 18 of Invention

| (1) | Monostearyltrimethylammonium chloride | 0.2(%) |
|---|---|---|
| (2) | Behenyl alcohol | 1.0 |
| (3) | Propylene glycol | 0.5 |
| (4) | Water (1) | 8.3 |
| (5) | Water (2) | 90.0 |

To (4) heated to 70° C. was added a mixture of (1) to (4) heated to and dissolved at the same temperature as indicated above, followed by agitating for emulsification and cooling to room temperature while agitating. After the cooling, (5) was added to the mixture at a normal temperature under agitation to obtain a composition.

Product No. 19 of Invention

| (1) | Monostearyltrimethylammonium chloride | 0.2(%) |
|---|---|---|
| (2) | Behenyl alcohol | 1.0 |
| (3) | Propylene glycol | 0.5 |
| (4) | Water (1) | 18.3 |
| (5) | Water (2) | 80.0 |

To (4) heated to 70° C. was added a mixture of (1) to (3) heated to and dissolved at the same temperature as indicated above, followed by agitating for emulsification and adding cooled (5) while agitating, thereby obtaining a composition.

Comparative Product No. 15

| (1) | Monostearyltrimethylammonium chloride | 0.2(%) |
|---|---|---|
| (2) | Behenyl alcohol | 1.0 |
| (3) | Propylene glycol | 0.5 |
| (4) | Water | 98.3 |

To (4) heated to 70° C. was added a mixture of (1) to (3) heated to and dissolved at the same temperature as indicated above, followed by cooling to room temperature while agitating, thereby obtaining a composition.

Comparative Product No. 16

| (1) | Monostearyltrimethylammonium chloride | 0.2(%) |
|---|---|---|
| (2) | Behenyl alcohol | 1.0 |
| (3) | Propylene glycol | 0.5 |
| (4) | Polyoxyethylene hardened castor oil 60EO | 0.5 |
| (5) | Water | 97.8 |

To a mixture of (1), (2), (3) and (4) which was heated to and dissolved at 70° C. was gradually added (5), which was heated to the same temperature level as indicated above, followed by emulsification and cooling to room temperature with agitation, thereby obtaining a composition.

TABLE 5

| Item | Composition | Good | Fair | Almost the Same | Fair | Good | Composition |
|---|---|---|---|---|---|---|---|
| Softness | Inventive Product 18 | 6 | 7 | 5 | 2 | 0 | Comparative Product 15 |
| Smoothness | | 6 | 9 | 3 | 2 | 0 | |
| Ease in Combing | | 7 | 9 | 3 | 1 | 0 | |
| Softness | Inventive | 2 | 11 | 5 | 2 | 0 | Comparative |

TABLE 5-continued

| Item | Composition | Good | Fair | Almost the Same | Fair | Good | Composition |
|---|---|---|---|---|---|---|---|
| | Product 19 | | | | | | Product 15 |
| Smoothness | | 2 | 11 | 6 | 1 | 0 | |
| Ease in Combing | | 3 | 12 | 6 | 2 | 0 | |
| Softness | Inventive Product 18 | 7 | 8 | 3 | 2 | 0 | Comparative Product 16 |
| Smoothness | | 7 | 10 | 2 | 1 | 0 | |
| Ease in Combing | | 7 | 9 | 4 | 0 | 0 | |

What is claimed is:

1. A hair rinse composition which comprises (A) 0.05 to 0.5 wt % of a cationic surface active agent, and (B) a second component selected from the group consisting of a higher alcohol, a glycerine mono fatty acid ester having a melting point not lower than 45° C. and mixtures thereof, said second component being present in said hair rinse in an amount of 3 to 15 times by weight to ingredient (A), and wherein said composition is produced by first forming a highly concentrated emulsified product comprising 0.4 to 34 wt % of ingredients (A) and (B), and thereafter diluting said concentrated product with water in the amount of 1 to 20 times by weight of said concentrated product.

2. The hair rinse composition according to claim 1, wherein said cationic active agent comprises at least one compound represented by the general formula (I)

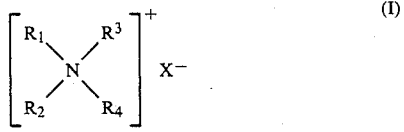

in which one or two of $R_1$, $R_2$, $R_3$, and $R_4$ independently represent a linear or branched alkyl or hydroxyalkyl group having from 8 to 22 carbon atoms, and the remaining $R_{1-4}$ substituents independently represent an alkyl group having from 1 to 3 carbon atoms, hydroxyalkyl group, benzyl group, or polyoxyethylene group in which the total number of moles of ethylene oxide added is not larger than 10, and X represents a halogen atom or alkylsulfate group having 1 to 2 carbon atoms.

3. The hair rinse composition according to claim 1 or 2, wherein said higher alcohol has a linear or branched alkyl or alkenyl group having from 12 to 26 carbon atoms.

4. The hair rinse composition according to claim I or 2, wherein said glycerine monofatty acid ester is represented by the general formula (II)

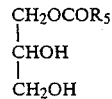

(II)

in which $R_5$ represents a saturated or unsaturated, linear or branched hydrocarbon group having from 11 to 23 carbon atoms.

5. A stable, emulsified hair rinse composition (A) 0.05 to 0.5 wt % of a cationic active agent, (B) a higher alcohol, or a glycerine monofatty acid ester having a melting point not lower than 45° C. and contained in an amount of 3 to 15 times by weight as large as ingredient (A), and (C) 0.1 to 5.0 wt % of a water-soluble polymer.

6. The hair rinse composition of claim 5, wherein said water-soluble polymer is selected from the group consisting of cellulose, cellulose derivatives, polyvinyl alcohol, polyvinylpyrrolodone, sodium polyacrylate, carboxylvinyl polymer, polyethyleneimine and mixtures thereof.

7. The hair rinse composition of claim 5, wherein said water-soluble polymer is of the general formula (II): T,0310 in which $R_6$–$R_{11}$ are independently represent hydrogen, $-(CH_2CH_2O)_m-H$, $-(CH_2CHhd 2CH_2O)_m-H$ (wherein m is an integer of from 1 to 5), $-CH_3$, $-CH_2H_5$, or $-COONa$, and n is an integer of from 5 to 5000.

8. A process for preparing the hair rinse composition of claim 1, comprising:
preparing a concentrated emulsion by adding, to a volume of water, 0.1 to 9% by weight of ingredient (A) and 3–50 times as much ingredient (B), said water being present in sufficient amount such that the total amount of ingredients (A) and (B) is 0.4–34 wt %, and heating said mixture under agitation;
thereafter, diluting said concentrated emulsion with water in an amount 1 –20 times the weight of said concentrated emulsion, said water being added in sufficient amounts such that the total content of ingredient (A) is 0.05–0.5 wt % of the total emulsion.

9. The process of claim 8, wherein said water is added to said concentrated emulsion in an amount 2-15 times by weight of the concentrated emulsion.

10. The process of claim 8 which further comprises adding, to said diluted emulsion, a water-soluble polymer selected from the group consisting of cellulose, cellulose derivatives, polyvinyl alcohol, polyvinylprrolidone, sodium polyacrylate, carboxylvinyl polymer, polyethyleneimine and mixtures thereof.

* * * * *

UNITED STATES PATENT AND TRADEMARK OFFICE
CERTIFICATE OF CORRECTION

PATENT NO. : 4,859,457

DATED : August 22, 1989

INVENTOR(S) : Toshio Suzuki, et al

It is certified that error appears in the above-identified patent and that said Letters Patent is hereby corrected as shown below:

Column 1, line 58, "an" should read --any--.

Column 3, lines 61-62, "ordinary" should read --ordinarily--;
    line 64, "are" should read --is--.

Column 4, line 28, "Low temperature stability" should be centered on a line as a heading.

Column 5, line 19 and 20, "After the cooling, water (2) was added to the mixture while agitating" should be deleted;

Column 5, Table I, last line, Rinsing Performance, under column 1 and column 2, please insert --    --.

Column 7, line 1, "Example 3" should read --Example 4--;

Claim 10, line 56, "polyvinylp-" should read --polyvinylpy--.

UNITED STATES PATENT AND TRADEMARK OFFICE
CERTIFICATE OF CORRECTION

PATENT NO. : 4,859,457

DATED : August 22, 1989

INVENTOR(S) : Toshio Suzuki, et al

It is certified that error appears in the above-identified patent and that said Letters Patent is hereby corrected as shown below:

Claim 7, line 29, "T,0310" should read

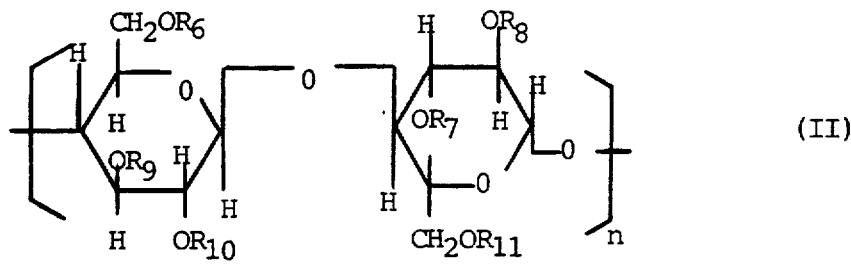

(II)

line 31, "-($CH_2$CHhd 2$CH_2$O)$_m$-H" should read

-- -($CH_2CH_2CH_2O)_m$-H --.

Signed and Sealed this

Twenty-sixth Day of February, 1991

*Attest:*

HARRY F. MANBECK, JR.

*Attesting Officer*     *Commissioner of Patents and Trademarks*